(12) United States Patent
Fredberg et al.

(10) Patent No.: US 6,440,083 B1
(45) Date of Patent: Aug. 27, 2002

(54) AIRWAY GEOMETRY IMAGING

(76) Inventors: Jeffrey J. Fredberg, c/o The Biomechanics Institute, 25 Bay State Rd., Boston, MA (US) 02215; Bruno Louis, c/o Inserm U296, 8 avenue du Géneral Sarrail, 94010 Créteil (FR)

(*) Notice: Subject to any disclaimer, the term of this patent is extended or adjusted under 35 U.S.C. 154(b) by 0 days.

(21) Appl. No.: 08/283,074

(22) Filed: Jul. 29, 1994

Related U.S. Application Data

(63) Continuation-in-part of application No. 07/808,907, filed on Dec. 17, 1991, and a continuation-in-part of application No. PCT/US92/09236, filed on Jun. 16, 1993.

(51) Int. Cl.$^7$ ............................................. A61B 5/085
(52) U.S. Cl. ...................................................... 600/533
(58) Field of Search ................................ 128/720, 725, 128/774, 780, 660.01, 660.02, 660.07, 662.03; 600/437, 438, 443, 459, 533, 538, 589, 593

(56) References Cited

U.S. PATENT DOCUMENTS 4,326,416 A  4/1982  Fredberg ..................... 73/597

FOREIGN PATENT DOCUMENTS

| FR | A 2 672 793 | 2/1991 |
| WO | WO 89/12423 | 12/1989 |
| WO | WO 91/12051 | 8/1991 |
| WO | WO 93/11703 | 6/1993 |

OTHER PUBLICATIONS

PCT International Search Report dated Sep. 17, 1993 PCT/US93/05819.
M. Cauberghs and K.P. Van de Woestijne, Mechanical Properties of the Upper Airway, 1983, pp. 335–342.
J.Y. Chung and D.A. Blaser, Transfer Function Method of Measuring In–Duct Acoustic Properties. I. Theory, 1980, pp. 907–908, 910–913.

93916599.9, Jan. 27, 1995, EPO communication.

Acoustic measurement of the respiratory system—an acoustic pneumograph, Miyakawa et al., Medical and Biological Engineering and Computing, vol. 14, No. 6, Nov. 1976, pp. 653–659., Stevenage GB.

(List continued on next page.)

*Primary Examiner*—William E. Kamm
(74) *Attorney, Agent, or Firm*—Fish & Richardson P.C.

(57) ABSTRACT

Apparatus provides an output signal characteristic of the geometry of a confined volume. There is a conduit with an open first end for exchanging acoustical energy with the confined volume. An electroacoustical transducer is coupled to the conduit for launching acoustical energy into the conduit towards the opening in the confined volume producing an incident wave and a reflected wave to form a wave field representative of the geometry of the confined volume. In one embodiment, the acoustical energy is launched into a sidewall of the tube. At least first and second pressure-wave-sensing transducers are mounted along the length of the conduit in spaced relationship for providing first and second transduced signals representative of the wave field at spaced locations in the conduit. A processor processes the first and second transduced signals to provide an output signal characteristic of the geometry of the confined volume. In one embodiment, the processor provides high-pass filtering of the impulse response.

33 Claims, 9 Drawing Sheets

OTHER PUBLICATIONS

Microcomputer–based system to calculate respiratory impedance from forced random noise data, Pelle et al., Medical and Biological Engineering and Computing, vol. 24, No. 5, Sep. 1986, pp. 541–544, Stevenage GB.

Instrumentation for Measuring Respiratory Impedance by Forced Oscillations, Pimmell et al., IEEE Transactions on BME, vol. 24, No. 2, Mar. 1977, pp. 89–93, New York, US.

Pelle et al, "Microcomputer–based system to calculate respiratory impedance from forced random noise data", Medical & Biological Engineering & Computing, vol. 24, No. 5, Sep. 1986, pp. 541–544.

Pimmel et al, "Instrumentation for Measuring Respiratory Impedance by Forced Oscillations", IEEE Transactions on BME, vol. 24, No. 2, Mar. 1977, pp. 89–93.

Miyakawa et al., "Acoustic measurement of the respiratory system—An acoustic pneumograph", Medical and Biological Engineering, vol. 14, No. 6, Nov. 1976, pp. 653–659.

J.Y. Chung and D.A. Blaser, Transfer Function Method of Measuring In–Duct Acoustic Properties. II. Theory, 1980, pp. 914–921.

K.P. Van de Woestijne, H. Franken, M. Cauberghs, F.J. Landser and J. Clement, A Modification of the Forced Oscillation Technique, 1976, pp. 655–660.

A.F. Seybert and D.F. Ross, Experimental Determination of Acoustic Properties Using a Two–Microphone Random–Excitation Technique, 1976, pp. 1362–1370.

Schroder, Determination of the Geometry of the Human Vocal Tract by Acoustic Measurement, 1967, pp. 1002–1010.

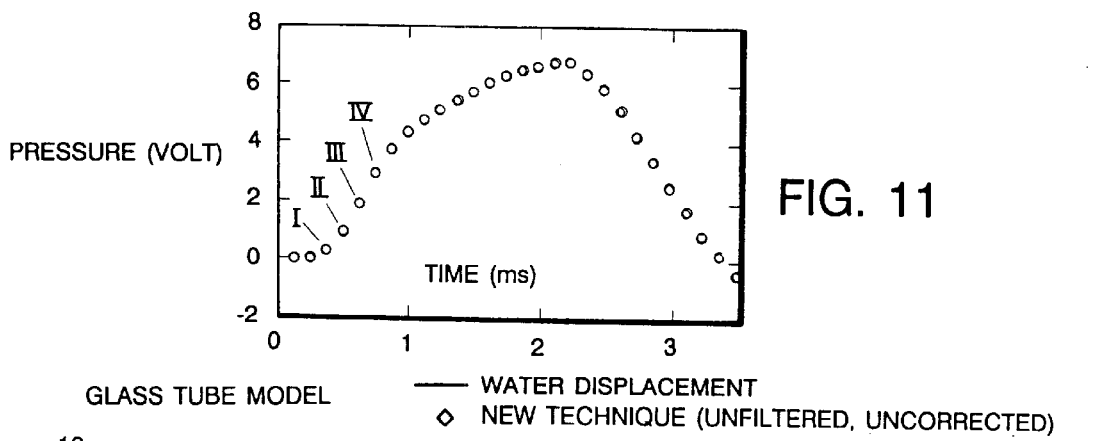
FIG. 11
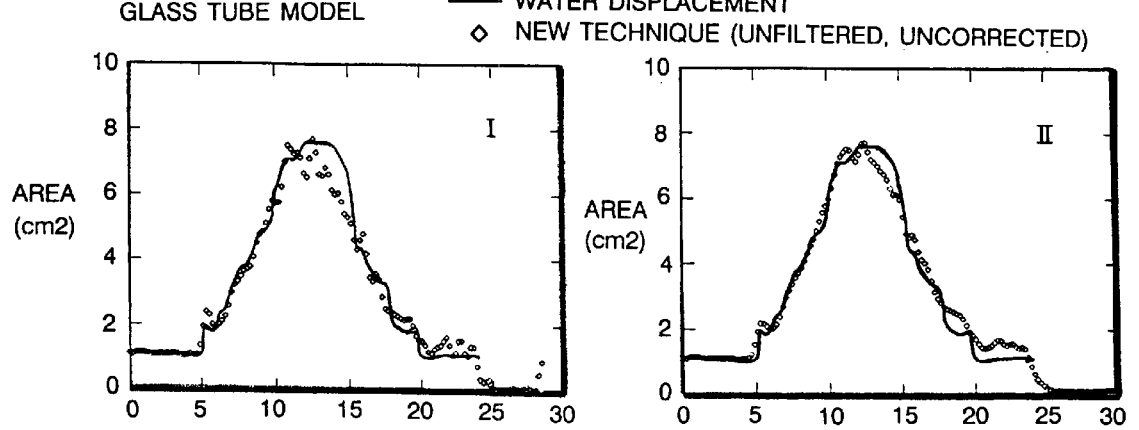
GLASS TUBE MODEL ——— WATER DISPLACEMENT
◇ NEW TECHNIQUE (UNFILTERED, UNCORRECTED)
FIG. 7
FIG. 8
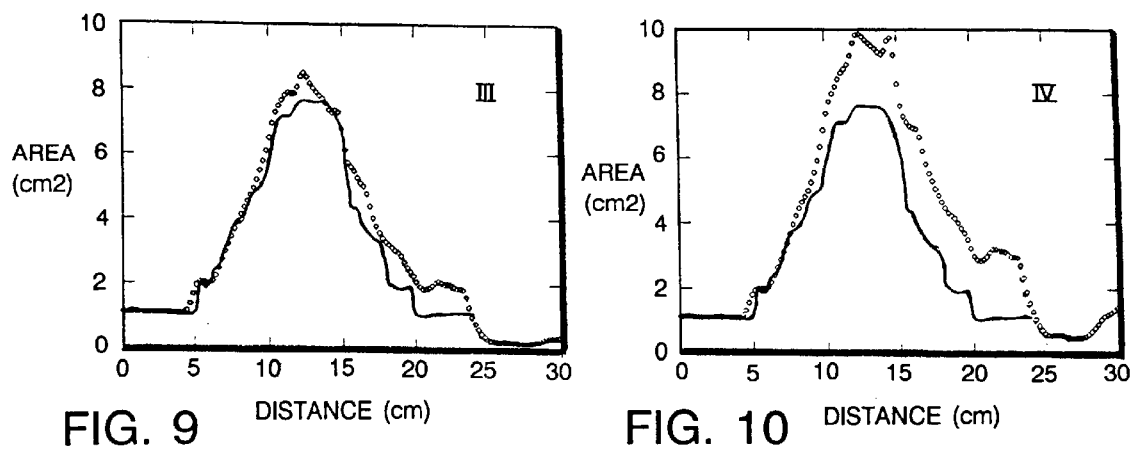
FIG. 9
FIG. 10

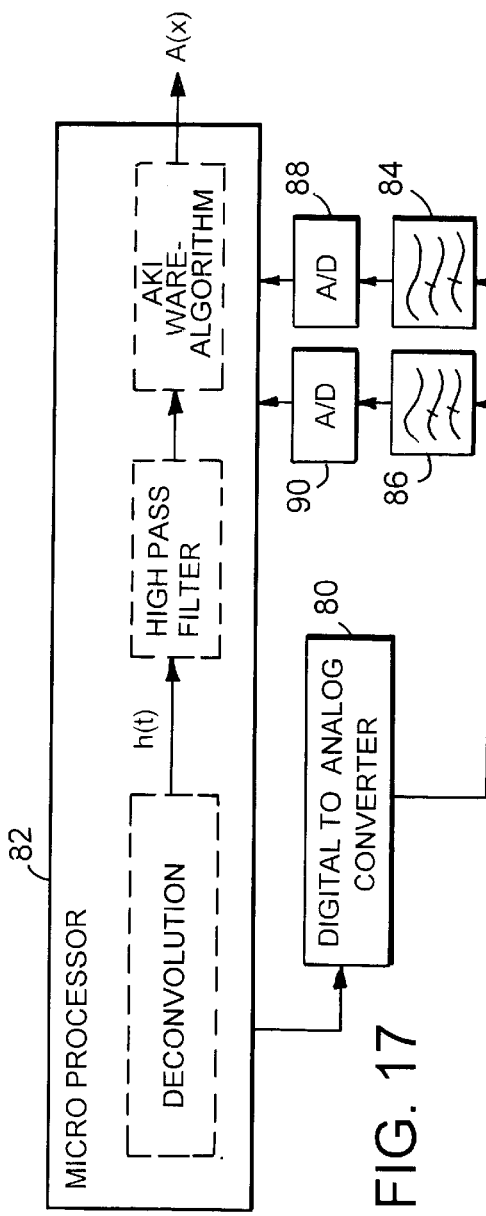
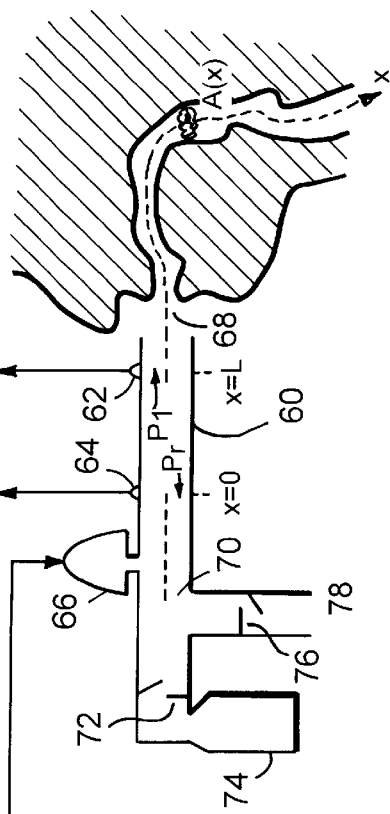
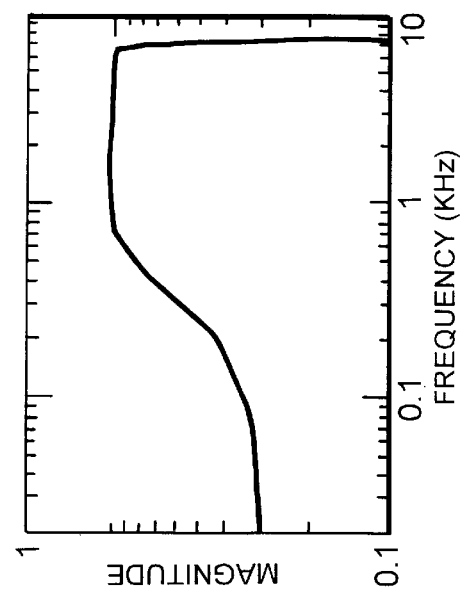
FIG. 17
FIG. 18

AIRWAY GEOMETRY IMAGING

This application is a continuation-in-part of application Ser. No. 07/808,907, filed Dec. 17, 1991 and entitled AIRWAY GEOMETRY IMAGING and a continuation-in-part of Application Ser. No. PCT/US92/09236, having an international filing date of Jun. 16, 1993 and international publication date of May 11, 1994 and entitled ACOUSTIC IMAGING, the subject matter of both such patent applications hereby being incorporated herein by reference.

This invention relates in general to imaging airway geometry and more particularly concerns noninvasively obtaining a signal representative of the cross-sectional area of an airway (e.g., oral, nasal, or pulmonary) of a subject (e.g., a person or an animal) using multiple spaced electroacoustical transducers.

A one-dimensional image of the cross-sectional area of an airway as a function of axial position along the airway may, be determined from acoustic reflections measured by a single electroacoustic transducer placed in a position remote from the airway opening. This image is referred to as an area-distance function and is represented by A(x) where x is the axial position along the airway.

Knowledge of the area-distance function, A(x), is useful in the diagnosis of pathologies associated with oral airways, larynx, pulmonary airways, and nasal airways, for example. These pathologies include but are not limited to obstructive sleep apnea, asthma, obstructive pulmonary disease, tracheal stenosis, and nasal septum deviation. Accurate information about the area-distance function is also useful in the study of airway growth and its disruption and sequelae of bronchopulmonary dysplasia in children, for example.

One approach toward using a single electroacoustic transducer is described in U.S. Pat. No. 4,326,416 granted Apr. 27, 1982, to Jeffrey J. Fredberg entitled ACOUSTIC PULSE RESPONSE MEASURING. A two-transducer approach is described in a paper of M. R. Schroeder entitled "Determination of the Geometry of the Human Vocal Tract by Acoustic Measurements" in J. Acoust. Soc. Am. 41(4), 1002-10 (1967).

According to the invention there is apparatus for providing an output signal characteristic of the geometry of a confined volume including a conduit for exchanging acoustical energy with the confined volume. The conduit has an open first end in communication with an opening in the confined volume. A transducer, such as a loudspeaker, is coupled to the conduit for launching acoustical energy into the conduit producing an incident wave towards the opening in the confined volume and a reflected wave to form a wave field in the conduit representative of the geometry of the confined volume.

In accordance with one feature of the invention at least one pressure wave sensing transducer, such as a microphone, is mounted along the length of a conduit. The pressure wave sensing transducer is mounted in spaced relationship to provide a transduced signal representative of the wave field. The conduit has a pair of open ends. One of the ends is open to the atmosphere, an environment at substantially atmospheric pressure, another instrument such as a flowmeter, volume meter (i.e., spirometer) or a ventilator. The other end is adapted for coupling to the confined volume. A transducer, such as a loudspeaker, is coupled to a sidewall of the conduit for launching acoustical energy into the conduit producing an incident wave towards the opening in the confined volume and a reflected wave to form a wave field in the conduit representative of the geometry of the confined volume. A processor processes the transduced signal to provide an output signal characteristic of the geometry of the confined volume, such as the cross-sectional area of the confined volume as a function of the distance from the opening in the confined volume.

In accordance with another feature of the invention at least first and second pressure wave sensing transducers, such as microphones, are mounted along the length of the conduit. The conduit may be either lossless (i.e., free of sound absorbing or acoustic energy absorbing material terminations), or may include sound absorbing material terminations. In either case, reflections from an end of the conduit are processed to provide a signal representative of the impulse response of the airway. The at least first and second pressure wave sensing transducers are mounted in spaced relationship to provide first and second transduced signals representative of the wave field. The conduit has a pair of open ends. One of the ends is open to the atmosphere, an environment at substantially atmospheric pressure, another instrument such as a flowmeter, volume meter (i.e., spirometer) or a ventilator. The other end is adapted for coupling to the confined volume. A transducer, such as a loudspeaker, is coupled to a sidewall of the conduit for launching acoustical energy into the conduit producing an incident wave towards the opening in the confined volume and a reflected wave to form a wave field in the conduit representative of the geometry of the confined volume. A processor processes the first and second transduced signals to provide an output signal characteristic of the geometry of the confined volume, such as the cross-sectional area of the confined volume as a function of the distance from the opening in the confined volume.

The process according to the invention includes connecting an open first end of the conduit to an opening in the confined volume, delivering acoustical energy into the conduit to provide incident and reflected waves that form the wave field in the conduit, transducing acoustic energy at spaced locations along said conduit to provide first and second transduced signals representative of said wave field at spaced locations in the conduit, and processing said first and second transduced signals to provide an output signal representative of the geometry of said confined volume. The second open end allows a portion of reflected wave energy to pass to the atmosphere, an environment at substantially atmospheric pressure, another instrument such as a flowmeter, volume meter (i.e., spirometer) or a ventilator.

The invention provides an output signal representative of airway geometry without calibration in apparatus that is relatively small and portable. The invention may be used for diagnostic and screening purposes in a confined area such as a laboratory, a doctor's office, a place of work, and at bedside. Additionally, the invention requires little or no cooperation by the subject being tested, facilitating its use in pediatric applications. Further, because the second end is opened to the atmosphere, an environment at substantially atmospheric pressure, another instrument such as a flowmeter, volume meter (i.e., spirometer) or a ventilator, the arrangement is more comfortable for the patient.

In accordance with still another feature of the invention, low frequency components in either the acoustic energy delivered to the conduit, or in the processing of the transduced signals, are removed by high-pass filtering. The high-pass filtering may be used with either a single pressure-wave-sensing transducer arrangement or the arrangement using at least first and second pressure-wave-sensing transducers. The high-pass filtering reduces errors associated with acoustic waves reflected by nonrigid airway walls without the necessity for a high acoustic-wave-speed gas, such as He—$O_2$. Thus, with the high-pass filtering, use of a more convenient gas, such as air, albeit of lower acoustic wave speed, may be used and still provide reduced, non-ridged airway wall associated errors.

Other features, objects, and advantages of the invention will become apparent from the following detailed description and from the claims when read in connection with the accompanying drawings in which:

Figure 12:
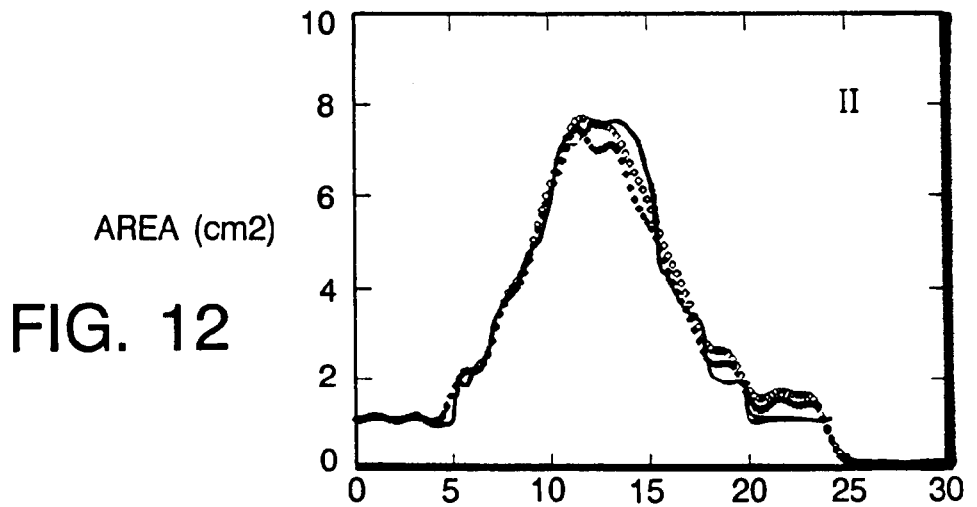
Figure 13:
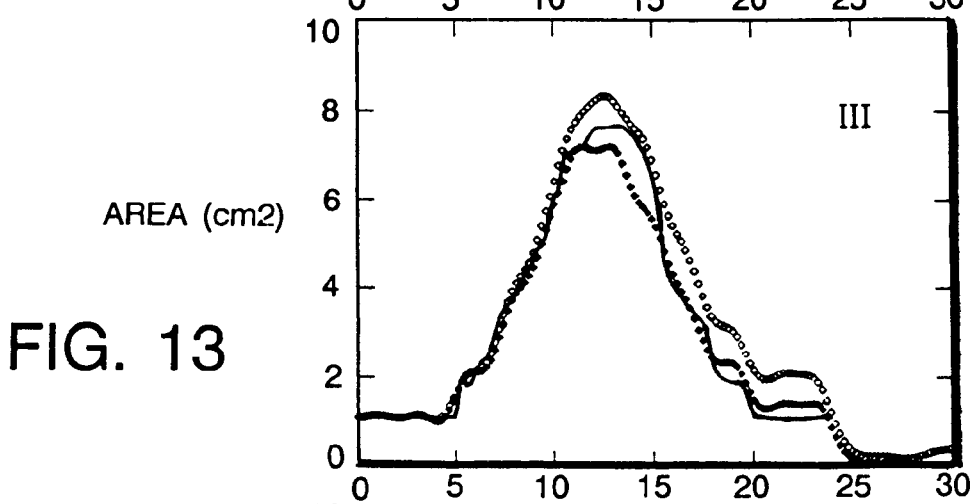
Figure 14:
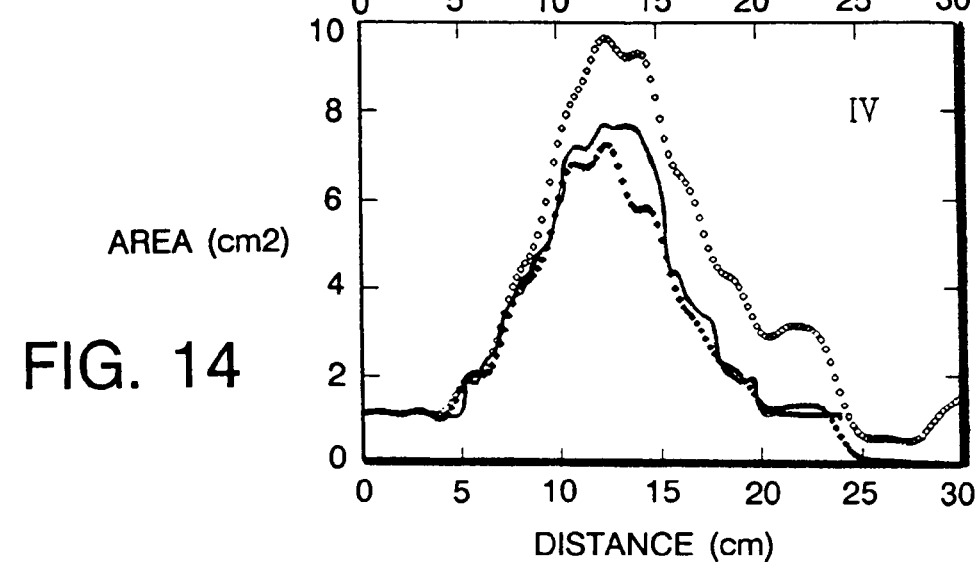
Figure 15:
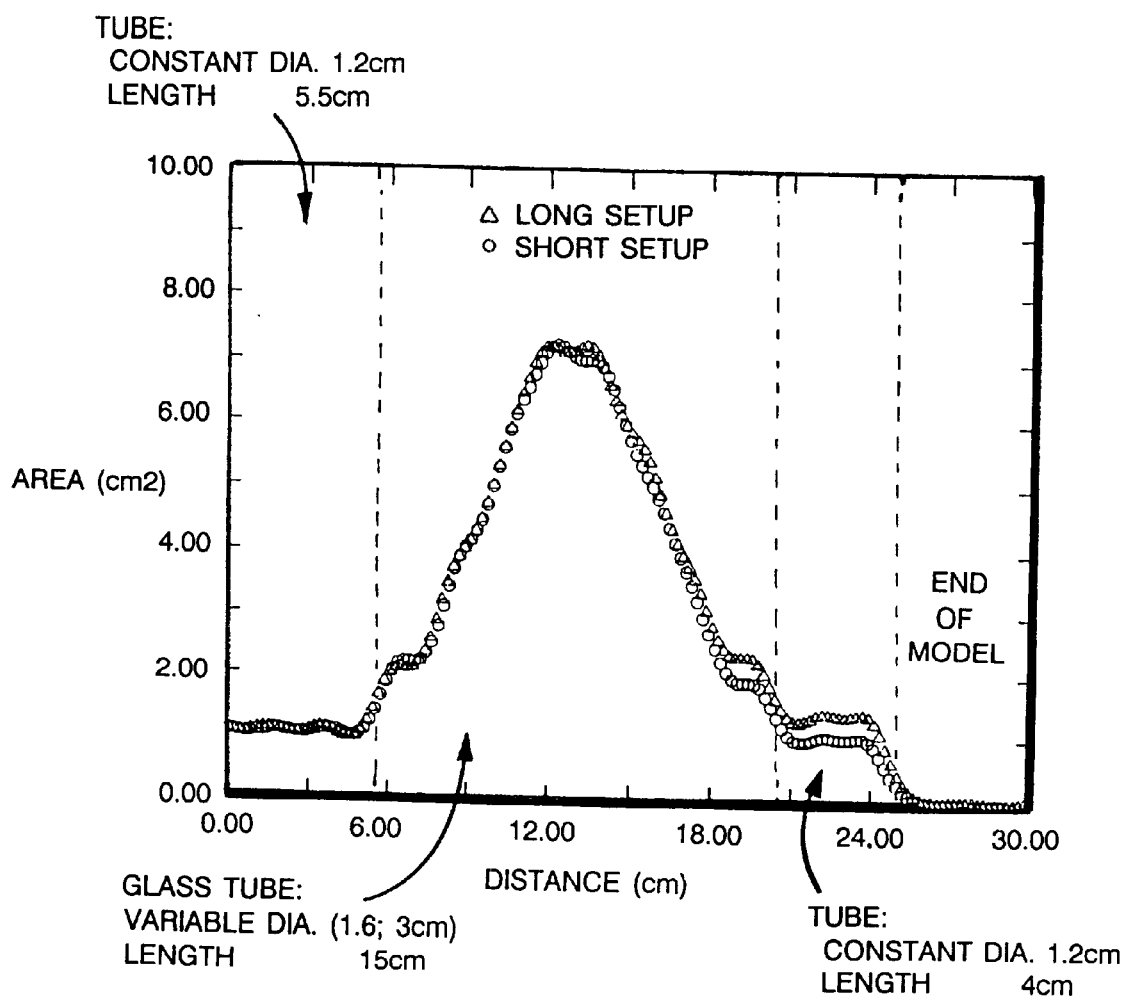
Figure 16:
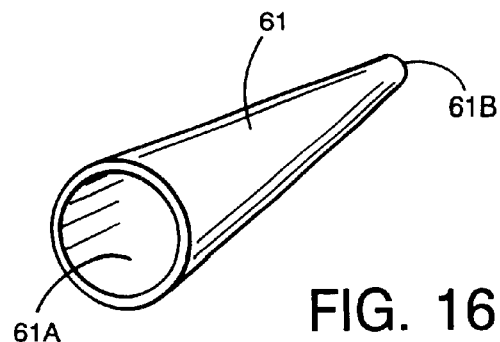
Figure 19:
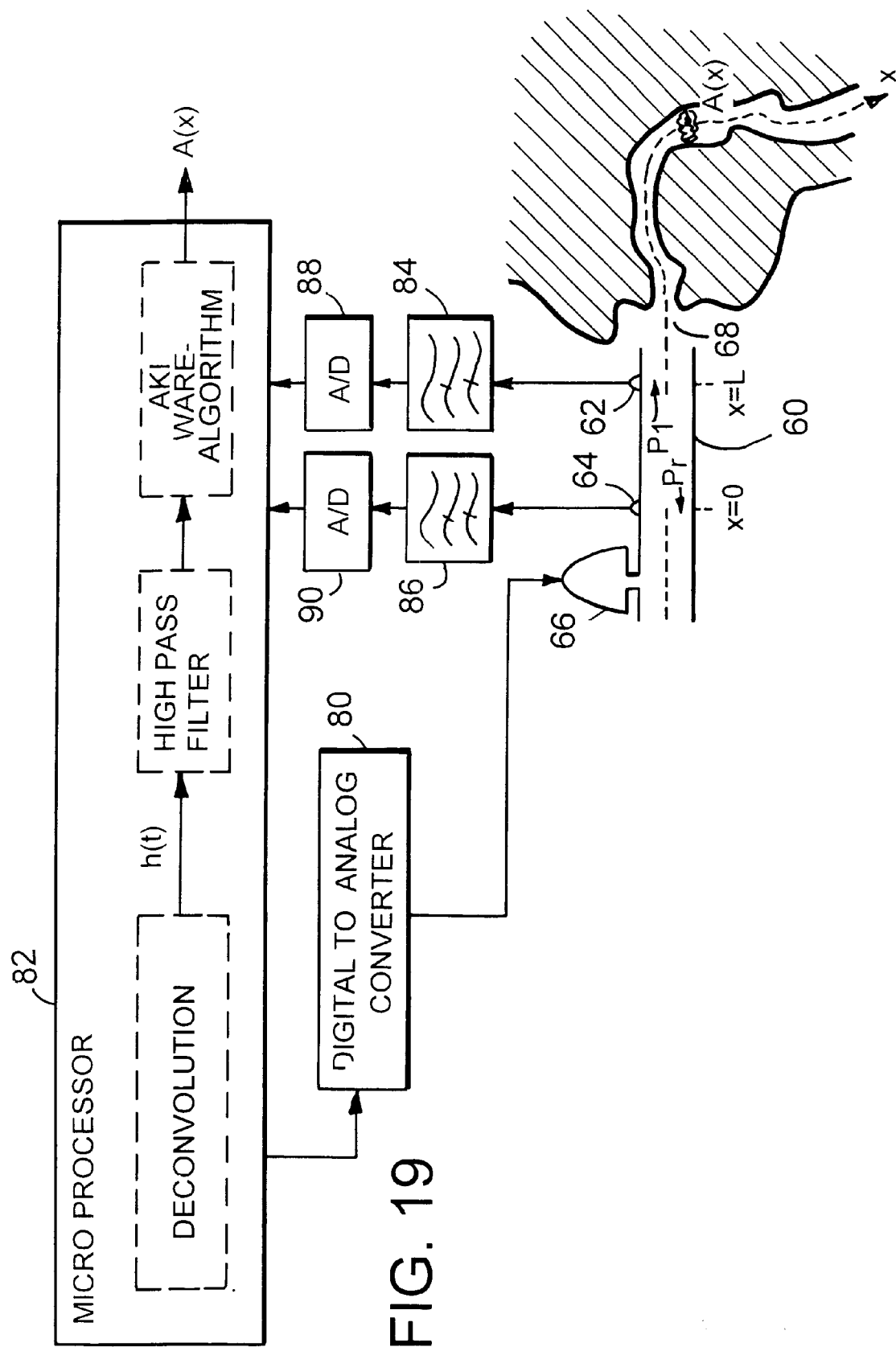
Figure 20:
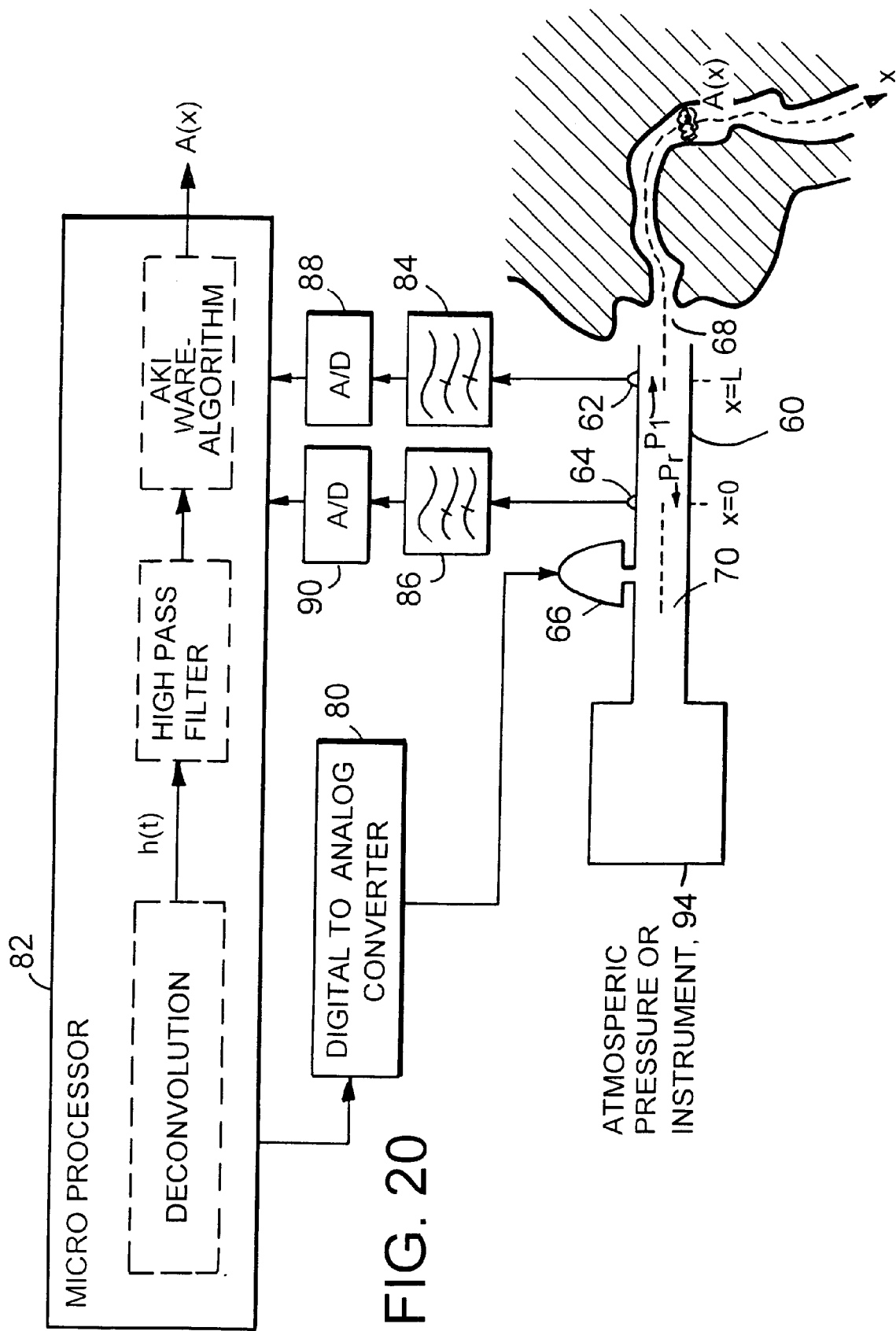

FIGS. 7, 8, 9, and 10 illustrate the effects of using a threshold to identify a first non-zero pressure value in computing the impulse response of the airway;

FIG. 11 is a plot of a pressure wave incident on the airway, various values of the pressure threshold being indicated on the plot;

FIGS. 12, 13, and FIG. 14 are plots of the area-distance function of the glass tube;

FIG. 15 shows plots of the area-distance function of the glass tube with variable diameter as determined by a dual-transducer system with a 15 cm tube and a dual-transducer system with a 10 cm tube;

FIG. 16 illustrates a disposable nasal coupling device;

FIG. 17 is a combined block-pictorial diagram illustrating the logical arrangement of a noninvasive, spaced-transducer system for imaging airway geometry according to an alternative embodiment of the invention;

FIG. 18 is a plot of the frequency response of a high-pass filter applied to the impulse response of the airway prior to determination of the area-distance function, A(X), by the Ware-Aki algorithm;

FIG. 19 is a combined block-pictorial diagram illustrating the logical arrangement of a noninvasive, spaced-transducer system for imaging airway geometry according to another alternative embodiment of the invention, and FIG. 20 is a combined block-pictorial diagram illustrating the logical arrangement of a noninvasive, spaced-transducer system for imaging airway geometry according to still another alternative embodiment of the invention.

Figure 1:
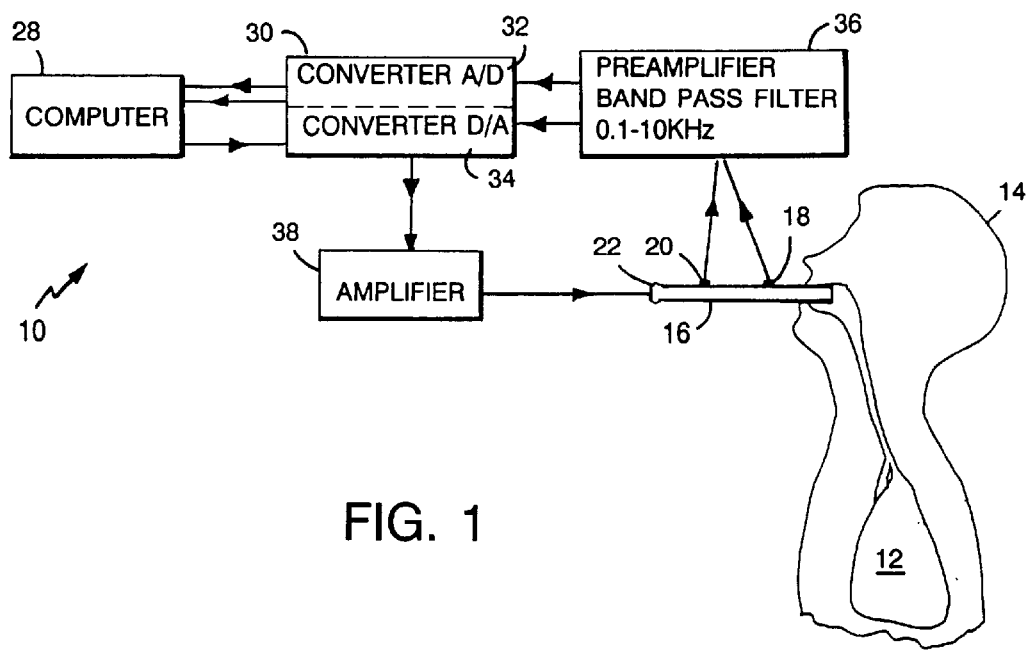
FIG. 1 is a combined block-pictorial diagram illustrating the logical arrangement of a noninvasive, spaced-transducer system for imaging airway geometry according to the invention.

Referring now to FIG. 1, a spaced-transducer system 10 for noninvasively obtaining a signal representative of the cross-sectional area of an airway 12 (e.g., a pulmonary airway) of a subject 14 (e.g., a person or an animal) includes a tube 16 with a diameter typically of 1.2 cm and a length typically of 15.0 cm. Two spaced pressure transducers 18, 20 (such as Endevco series 8510 B microphones) are mounted in tube 16 with their pressure sensing heads flush with the inner tube wall in order to reduce parasitic acoustic reflection. A loudspeaker 22 (such as Sony model MDR 434) is connected to one end of the tube 16. The other end of tube 16 is inserted in the airway opening of the subject. Transducers 18, 20 are typically separated by 10.25 cm, and transducer 18 is located typically 2.0 cm from the airway opening.

A microcomputer 28 (such as Compuadd model 320 with an Intel 80386 microprocessor operating at 20 MHz) is coupled to converter module 30 having a 12-bit analog-to-digital (A/D) converter 32 with a sampling period typically of 24.0 $\mu$s and a 12-bit digital-to-analog (D/A) converter 34 coupled to preamplifier 36 typically with a band-pass filter having a passband from 0.1 kHz to 10.0 kHz (such as Tektronix model AM 502) that is coupled to transducers 18 and 20. D/A converter 34 is coupled to loudspeaker 22 through amplifier 38.

Figure 2:
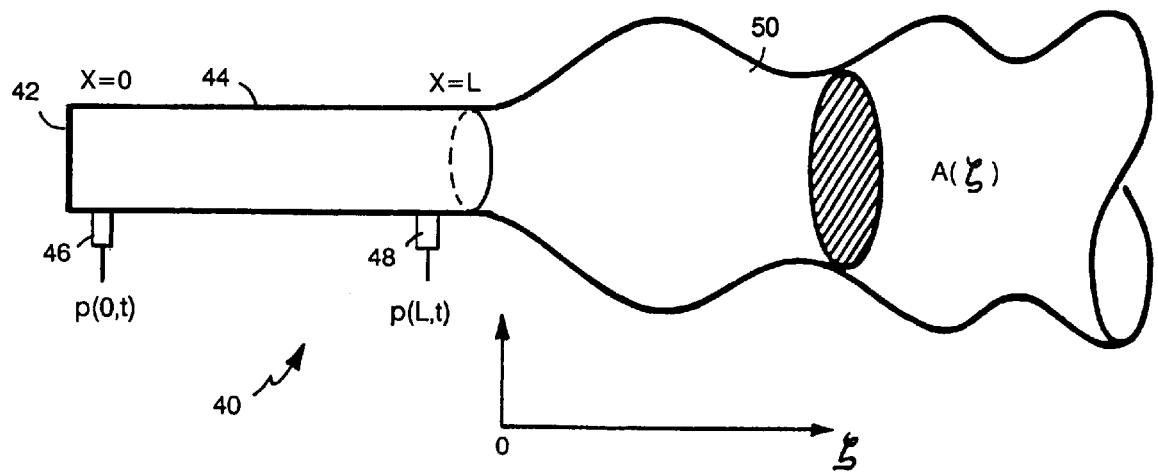
FIG. 2 is a simplified diagram illustrating the spaced-transducer system.

The mode of operation will now be described. Referring to FIG. 2, a simplified assembly 40 includes loudspeaker 42, tube 44 of length L, first transducer 46 located at x=0 where x is the axial position along tube 44, second transducer 48 located at x=L, and airway 50 (e.g., an oral, nasal, or pulmonary airway) of a subject.

Loudspeaker 42 launches a one-dimensional essentially lossless acoustic wave into tube 44. The launched incident wave travels through tube 44 and into airway 50. A reflected wave, or echo, representative of gradients in the acoustic impedance in the airway then propagates back through tube 44 towards loudspeaker 42. Transducers 46 and 48 provide transduced electrical signals representative of the incident and reflected waves for processing by computer 28.

Referring to FIG. 1, microcomputer 28 generates a digital probe signal converted to an analog signal by D/A converter 34, and amplified by amplifier 38 to drive loudspeaker 22 and launch the incident probe acoustic wave. The transduced outputs from transducers 46 and 48 are band-pass filtered by preamplifier 36 and then converted by A/D converter 32 into digital signals. Microcomputer 28 stores these digital signals.

Microcomputer 28 processes these stored digital signals to provide an output signal A(x), i.e., a one-dimensional image of the cross-sectional area of airway 50 as a function of axial position, x, along airway 50. Computer 28 preferably processes these signals in accordance with the Ware-Aki algorithm ("Continuous and Discrete Inverse-Scattering Problems in a Stratified Elastic Medium. I. Plane Waves at Normal Incidence", J. Acoust. Soc. Am., 54, 4, 911–921, 1969, incorporated herein by reference) to provide the area distance function, A(x), from the impulse response of airway 50, h(t). The relationship between the pressure field and h(t) may be derived as follows. The pressure field within the tube in the domain $0 \leq x \leq L$ can be described as the superposition of two one-dimensional waves propagating with the same wave speed but in opposite directions as given by $$p(x,t)=p_r(x,t)+p_1(x,t) \quad (1)$$

where t is time, $p_r$ is the incident wave propagating to the right (i.e., from x=0 towards x=L), and $p^1$ is the reflected wave propagating to the left (i.e., from x=L towards x=0). The pressure conditions at x=0 and x=L are given by $$p_1(L,t)=p_r(L,t)*h(t) \quad (2)$$

and $$p_r(0,t)=p_1(0,t)*s(t) \quad (3)$$

where s(t) is the impulse response of any device, opening or loudspeaker at the second end of the tube and * denotes the convolution operation. Given that a one-way propagation delay is $\tau=L/v$ where v is the velocity of sound, the following relationships exist:

$$p_1(0,t)=p_1(L,t-\tau) \quad (4)$$

$$p_r(L,t)=p_r(o,t-\tau). \quad (5)$$

Equations (1) through (5) may be combined by mathematical techniques well-known in the art (e.g., the Fourier transform, the inverse Fourier transform, and algebra) to yield $$h(t)*\{p(0,t)-p(L,t-\tau)\}=p(L,t-\tau)-p(0,t) \quad (6)$$

and $$h(t)*s(t)=\delta(t-2\tau) \quad (7)$$

Equation (7) indicates that both waves propagate with an equal, non-zero delay. In equation (7), the symbol δ denotes the well-known impulse function which is sometimes called the delta function. Equation (6) identifies the relationship between the pressure field and h(t).

Equation (6) may be discretized by the Riemann sum approximation to yield $$h(n\Delta t)=\{1/p(0,0)\}\{p(L,(m+n)\Delta t)-p(0,n\Delta t)\}-\{\Sigma h((n-k)\Delta t)/p(0,0)\}\{p(0,k\Delta t)-p(L,(k-m)\Delta t)\} \quad (8)$$

where Δt is the sampling duration of the time discretization, n is the set of integers 1, 2, 3, etc., m is an integer such that τ=mΔt, p(0,0) denotes the first non-zero pressure value at x=0, k is the index of summation, and the lower and upper limits of summation are, respectively, k=1 and k=n.

An advantageous feature of the final result characterized by Equations (6) and (8) is that neither equation contains the quantity s(t). As a result, desired output signals provided through processing in accordance with these equations do not depend on the reflection condition at the second end of the tube. Such reflections are taken into account implicitly when processing signals in accordance with Equations (6) and (8). It is therefore unnecessary to suppress such reflections by terminating the second end in sound absorbing material, and rereflected energy from the second end may be usefully processed according to the invention.

In brief summary, microcomputer 28 processes the stored digital data signals representative of the transduced signals from the spaced-transducers to provide a signal representative of the impulse response of airway 50, h(t), according to equation (8). Microcomputer 28 then processes the signal h(t) in accordance with the Ware-Aki algorithm to provide a signal, A(x), representative of the geometry of airway 50.

The wave propagation in tube 44 itself may be assumed lossless. Thus, while the process and algorithm are adapted for use with a conduit having sound absorbing material in it, here tube 44 is free of sound-absorbing or acoustic energy-absorbing material. It should be understood, however, that the conduit may be either lossless (i.e., free of sound absorbing or acoustic energy absorbing material termination), or may include sound absorbing material terminating the second end. In either case, reflections from an end of the conduit are processed to provide a signal representative of the impulse response of the airway. The early portions of the transduced pressures at x=0 and x=L are then identical except for the propagation delay t. Microcomputer 28 may determine the propagation delay by minimizing mean square differences between the transduced signals in the early part of their respective transients. The relative gain of the transducers may be determined in a similar manner. To obtain sufficient time resolution, microcomputer 28 preferably interpolates the transduced signals to achieve an effective sampling period of 0.75 µs (i.e., Δt=0.75 µs).

Equation (8) requires preferably the propagation delay to be an integral multiple of the sampling period Δt, i.e., τ=mΔt. Microcomputer 28 preferably interpolates and resamples digitized transduced signals such that the propagation delay corresponds to 24 time steps, i.e., τ=24Δt. This value of the propagation delay corresponds to a spatial step increment of about 0.2 cm.

In providing h(Δt) in accordance with equation (8), the first non-zero pressure value p(0,0) is preferably larger than some minimal threshold value to maintain stability. The pressure values occurring before this first threshold pressure are initially neglected to obtain a first approximation of h(t). To deemphasize errors that may be introduced by the threshold it is advantageous to provide a corrected h(Δt) characterized by increased stability and accuracy by convolving the first approximation of h(t) with the digitized pressure values occurring prior to the first non-zero pressure (i.e., the pressure values that were initially neglected).

Microcomputer 28 then preferably bandpasses the sequence of discrete values h(nΔt) that represents the impulse response of the airway h(t) with a digital, linear-phase, finite impulse response (FIR) filter having a passband from 0.01 kHz to 9 kHz to attenuate physiologic noise associated with breathing, artifacts associated with airway wall nonrigidity, instability of the impulse response, h(t), and artifacts associated with acoustic cross-modes.

Microcomputer 28 then processes the corrected h(Δt) signal in accordance with the Ware-Aki algorithm to provide an output signal representative of the area-distance function, A(x), of the airway graphically represented.

Figure 3:
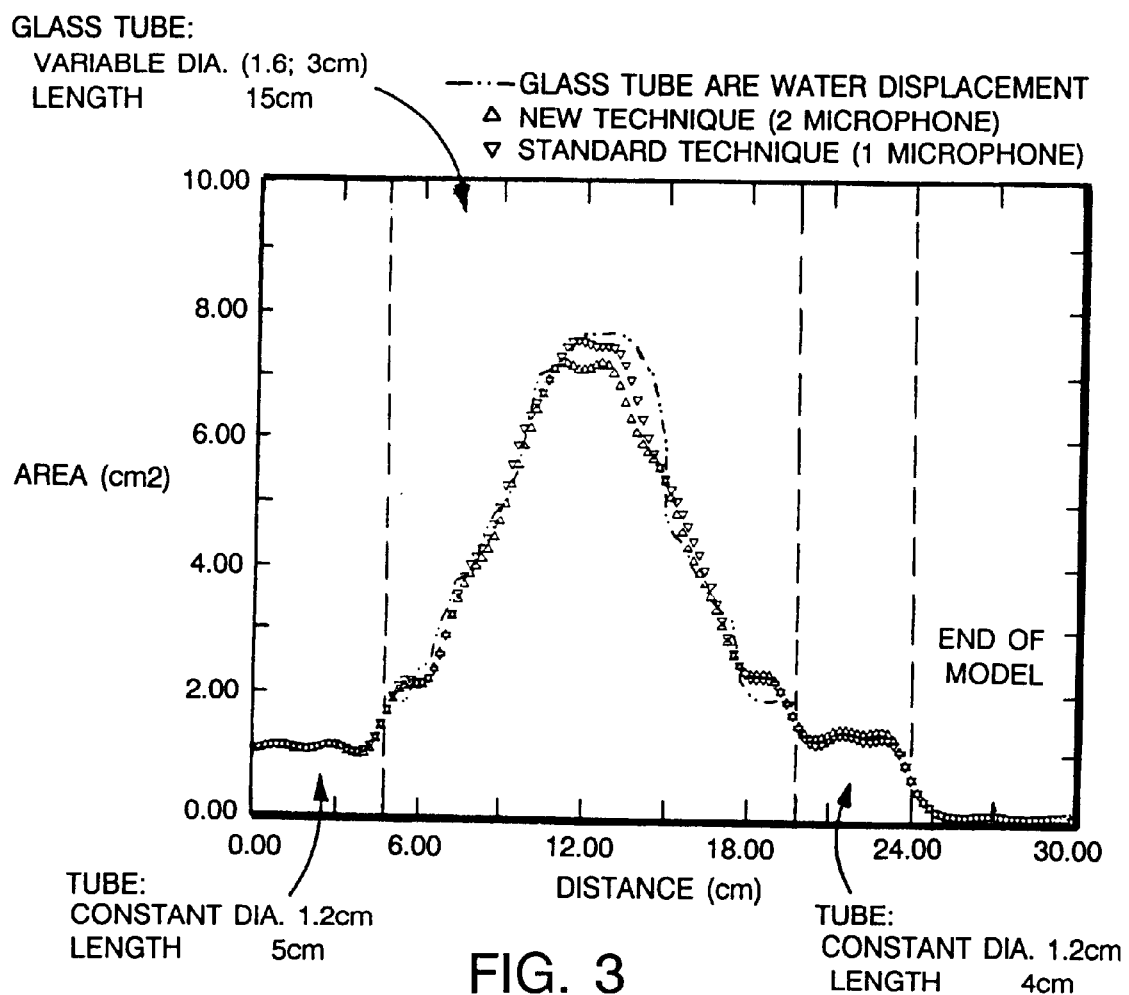
FIG. 3 shows plots of an area-distance function of a glass tube with variable diameter as determined by the dual-transducer system, a water displacement method, and a single-transducer system.

An exemplary embodiment of the invention substantially as shown in FIG. 1 provided a signal characteristic of the area-distance function of an axis-symmetric glass tube with variable diameter and a known area-distance function. FIG. 3 is a graphical representation of this signal compared with corresponding signals obtained by (1) a water displacement method and (2) a single-transducer system of the type described in U.S. Pat. No. 4,326,416.

The water displacement method involved gradually injecting water into a model/cast by a calibrated syringe and measuring the incremental relationship of water column height to water volume injected with a pressure transducer. The cross-sectional area of the water plane is equal to the volume increment divided by the height increment.

The single-transducer system was an existing noninvasive system for obtaining the cross-sectional area of an airway that included a tube with a diameter of approximately 5.0 cm and a minimum length of about 1.0 m; a single pressure transducer mounted in the tube; a sound source located in approximately the middle of the tube; and equipment to generate the sound, process the data recorded by the transducer, and display the processed data.

In FIG. 3, the origin of the distance axis corresponds to the location of the second transducer, i.e., x=L in FIG. 2. All three measured functions correspond substantially to the known area-distance function of the glass tube.

Figure 4:
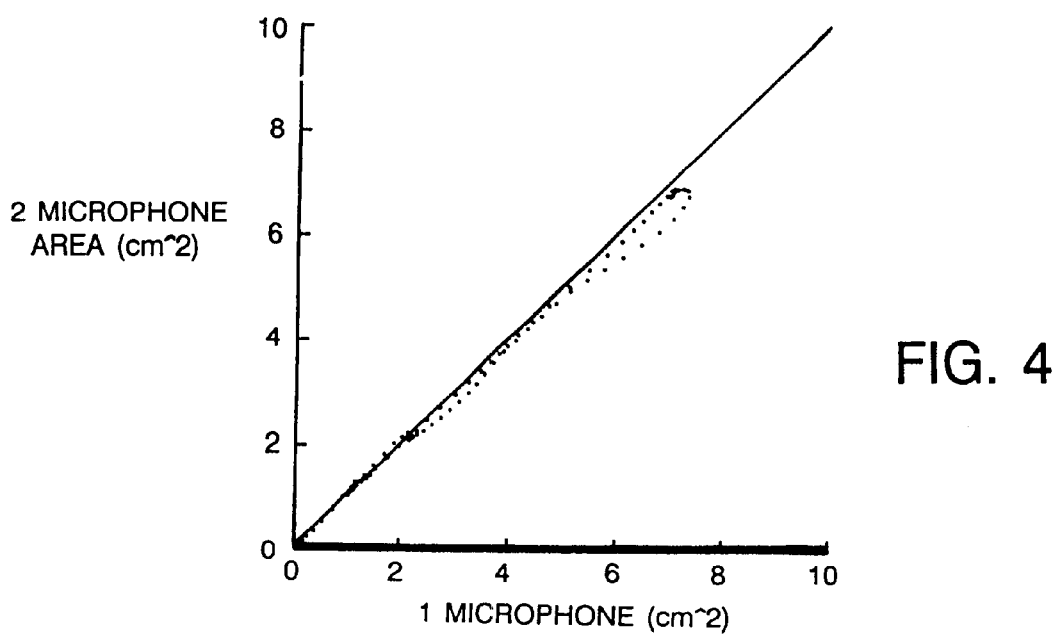
FIG. 4 is a comparison between the dual-transducer system and the single-transducer system.

Referring to FIG. 4, there is shown a graphical representation of departures from correspondence between the measurements of the system of FIG. 1 and the prior art single-transducer system. The correlation coefficient is above 0.998.

Figure 5:
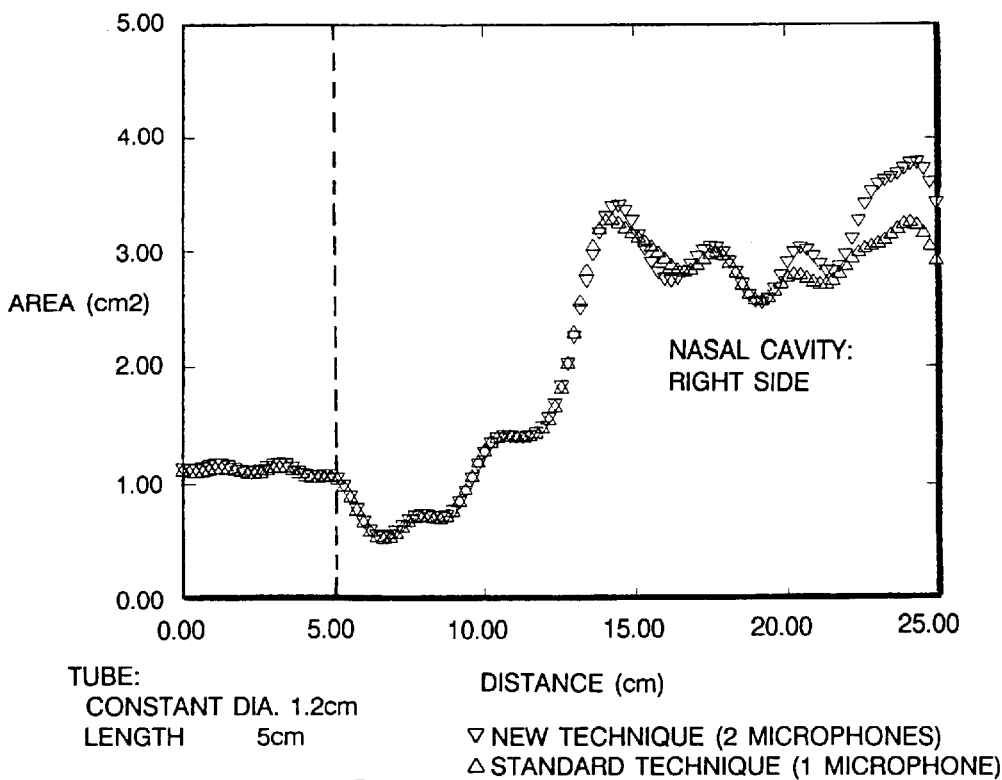
FIGS. 5 and 6 show plots of an area-distance function of the right and left sides of a nasal cavity cast as determined by the dual-transducer system and the single-transducer system, respectively.
Figure 6:
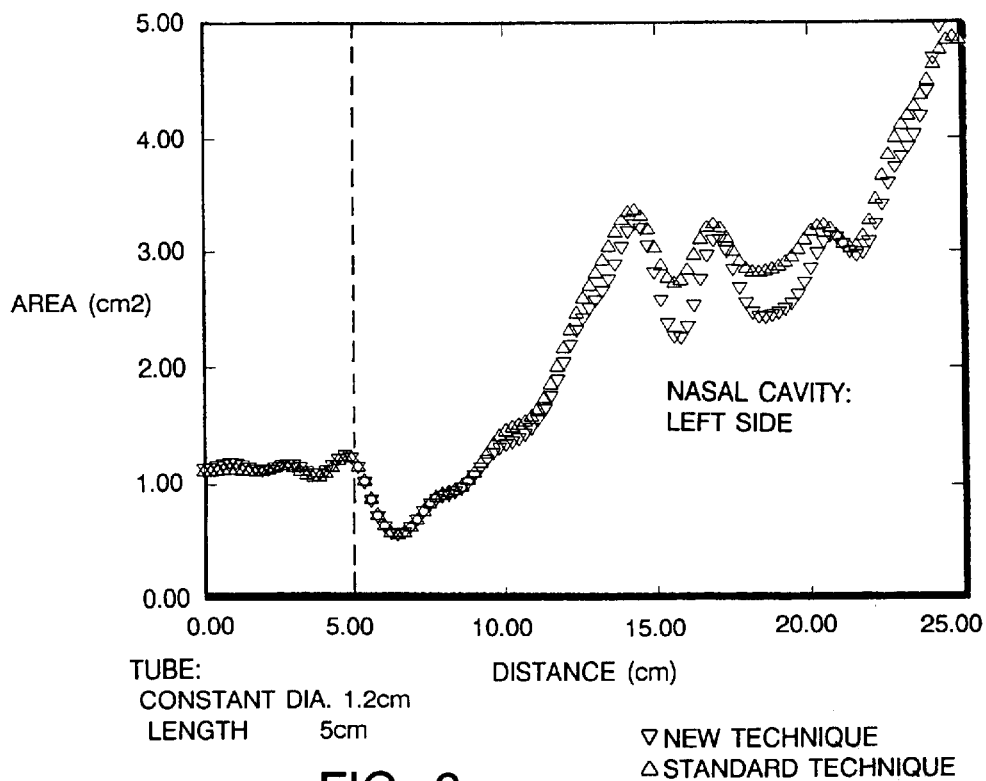

The system according to the invention and the prior art single-transducer system also provided signals representative of the area-distance function of a nasal cavity of a person. During the measurements, the person breathed slowly and spontaneously through the mouth. FIGS. 5 and 6 show these functions for right and left nasal cavities, respectively. As in FIG. 3, the origin of the distance axis corresponds to the location of the second transducer, i.e., x=L in FIG. 2. The function signals are substantially the same through 10 cm.

Referring to FIGS. 7–10, there are shown graphical representations of area as a function of distance using the data represented in FIG. 3 for comparing area function through water displacement compared with measurements according to the invention for threshold values I, II, III and IV, respectively, of FIG. 11 graphically representing pressure as a function of time. Closest correspondence between the area function through water displacement and according to the invention is shown in FIG. 8 using threshold level II.

Referring to FIGS. 12, 13 and 14, there are shown graphical representations of the area functions provided according to the invention compared with the area function derived from water displacement based on the impulse response filtered, but uncorrected, and the corrected impulse response filtered for threshold values II, III and IV, respectively.

It was discovered that the first non-zero pressure threshold is preferably approximately 100 times larger than the "noise floor" created by all noise sources combined to achieve adequate stability and accuracy.

Referring to FIG. 15, there is shown the area-distance function of an axially-symmetric glass tube with variable diameter provided by the invention with 15 cm (long setup) and 10 cm long (short setup) tubes, respectively. As in FIGS. 3 and 5–10, the origin of the distance axis corresponds to the location of the second transducer (i.e., x=L in FIG. 2); however, to obtain the same distance origin, the function provided using the long tube was shifted by 0.5 cm. These results show that the invention may provide good results with different tube lengths.

Referring to FIG. 16 there is illustrated a disposable nasal coupling device 61 having an input end 61A that attaches to the output end of tube 16 and an output end 61B for insertion into a nostril. Nasal coupling device 61 may have output ends of different sizes for snug engagement with the inside of nostrils of different sizes. Its internal area contour is such that impedance matching between subject and apparatus is maintained with maximum acoustic energy transmission. Similarly there may be disposable mouth coupling devices with output ends of different sizes for snugly engaging mouths of different sizes.

Reference is also made to an article entitled "Airway area by acoustic reflection: the two microphone method" by B. Louis, G. M. Glass, B. Kresen, and J. J. Fredberg, published in the Journal of Biomechanical Engineering (J.Biomech. Eng.) 115:278–285, 1993, the contents of which are hereby incorporated herein by reference.

Referring now to FIG. 17 another two-microphone arrangement is shown. Here, however, instead of mounting the loudspeaker 22 into the distal end of conduit, or tube 16, as in FIG. 1, or mounting the loudspeaker 42 into the distal end of tube 44, as in FIG. 2, the loudspeaker 66, is mounted to launch acoustical energy waves into a sidewall of conduit, or tube 60, as shown. Again tube 60, like tube 16 (FIG. 1) and tube 44 (FIG. 2) may either be free of, or not free of, sound-absorbing or acoustic-energy-absorbing material. Here tube 60 is 30 cm long and has an inside diameter of 1.89 cm. The tube 60 is made to accommodate two flush-mounted pressure transducers 62, 64 (here Endevco series 8510b) and the loudspeaker 66 (here a model PD-5VH, Atlas Sound, Parsippany, N.J.). The transducers 62, 64 are separated by here, 6.9 cm; the nearest one thereof, here transducer 62 being 5 cm from the airway opening 68, and the other one, here transducer 64 being 6 cm from the loudspeaker 66. The distal end 70 of tube 60 is coupled, via a first one-way valve 72, to a gas tank 74, and, via a second one-way valve 76, to the atmosphere 78, as shown. With such an arrangement, the patient is able to spontaneously breath in the gas contained in the tank 74 via one way valve 72, while being able to easily exhale directly to the atmosphere 78 via one way valve 76. Here the gas maybe either air or 80%He–20%$O_2$, although in the case of air, the tank 76 may be eliminated and the tube 16 need have a single distal end opened to the atmosphere, as will be described in connection with FIG. 19 or to an environment at substantially atmospheric pressure, another instrument such as a flowmeter, volume meter (i.e., spirometer) or a ventilator, as will be described in connection with FIG. 20.

The horndriver loudspeaker 66 is driven, via an analog-to-digital converter 80, by a signal generated by microprocessor 82. The output signals produced by the transducers 62, 64 are fed to analog band-pass filters 84, 86. Here, such filters 84, 86 are four-pole filters. The cutoff frequency of the filters 84, 86 are here 0.1–5 kHz, when air is used, and 0.1–10 kHz, when He—$O_2$ is used. The high-pass filtering (i.e., above 5 kHz, for air and above 10 kHz for He—$O_2$) of the band-pass filters 84, 86 tends to eliminate physiological noise associated with patient breathing. The low-pass filtering (i.e., below 0.1 kHz) tends to reduce the importance of artifacts associated with acoustic cross modes described in an article entitled "Non-invasive inference of airway network geometry from broadband lung reflection data" by R. S. Sidel and J. J. Fredberg, published in the Transactions of the American Society of Mechanical Engineers, Journal of Biomechanical Engineering (Trans. ASME J. Biomech. Eng.) 100:131–138, 1978. The output signals produced by the band-pass filters 84, 86 are fed to analog-to-digital converters 88, 90, respectively, as shown. Here, the analog-to-digital converters 88, 90 are twelve-bit converters with a sampling period of 24 microseconds. The digitized signals are then fed to the microprocessor 82 for computation of the impulse response h(t), as described above. The pressure data were interpolated and reassembled with a sampling frequency, f, such that the spatial step increment, $c_o \Delta/2$ was ~0.4 cm, where $c_o$ is the speed of sound. The stability of the time domain deconvolution algorithm was described in the above referenced article entitled "Airway area by acoustic reflection: the two microphone method". As noted above, low-pass filtering is used to minimize the stability problem associated with the deconvolution algorithm. Here, the low-pass filter cutoff frequencies are 7 kHz with air and 9 kHz with He—$O_2$. Such filtering is performed by finite impulse response (F.I.R.) digital filtering performed in the microprocessor 82, as described above. The computed impulse response, h(t), was analyzed by the Ware-Aki algorithm, as described above, to construct the airway area function, A(X).

As described in "Reproducibility and accuracy of airway area by acoustic reflection", by Brooks et.al., published in J. Appl. Physiol, 57:777–787, 1984 and "Airway from acoustic reflection measured at mouth", by Fredberg, et. al., in J. Appl. Physiol 48:749–758, 1980, nonrigidity of the airway wall leads to an overestimation of, or error in, the estimated tracheal area estimated by acoustic reflections with use of air. As described in these articles, this bias (i.e., error or overestimation), can be minimized by using a gas with a high wave speed, such as He—$O_2$; however, the use of He—$O_2$ is less convenient than air. Here, in order to reduce the importance of the wall nonrigidity artifact, a numerical high-pass filtering of the impulse response, h(t), is provided by the microprocessor 82. Such high-pass filtering of the impulse response, h(t), reduces that part of the impulse response, h(t), frequency spectrum (i.e., reduces the low frequencies) where the influence of wall compliance, or nonrigidity, is greatest. The high-pass filtering of the impulse response, h(t), is here a linear phase finite impulse response (F.I.R.) filter having a 125-point Hamming window. The optimum cutoff frequency depends on the wall compliance characteristics. A 250 Hz cutoff frequency is sufficient to minimize wall nonrigidity artifact in a pulmonary airway. Further, the filter tends to eliminate physiological noise due to breathing and variability in wall compliance. Moreover, because the high-pass filtering is introduced after the computation of the impulse response, h(t), such high-pass filtering may be used in both a one microphone and two microphone arrangement.

As noted above, here the cutoff frequency of the high-pass filtering of the impulse response, h(t), is here in the order of 250 Hz. Thus, as also noted above, because low-pass filtering is used to minimize the stability problem of the deconvolution algorithm (i.e., a cutoff frequency of 7 kHz with air and cutoff frequency of 9 kHz with He—$O_2$), the filtering provided by the microprocessor 82 is, in effect passband filtering having cutoff frequencies of 250 Hz and 7 kHz with air, as shown in FIG. 18, and cutoff frequencies of 250 hZ with He—$O_2$.

While preferably the high-pass filtering is performed on the impulse response, h(t), alternatively, high-pass filtering of the pressure data, i.e., on the signal used to drive the horndriver loudspeaker 66. In such case, the microprocessor 82 would provide the high-pass filtering to the horndriver loudspeaker 66 drive generating signals.

In view of the foregoing, and referring to FIG. 19, apparatus is shown which enables: (1) the use of a relatively short conduit, or tube (because of the use of at least two side-mounted pressure-wave transducers, or microphones); (2) the convenient use of air, albeit a relatively low acoustic-wave-velocity gas (because of the high-pass filtering, preferably of the impulse response, h(t), used to reduce the nonrigid wall effects on the low frequency components); and, (3) more comfortable use by the patient (because the side mounted acoustic energy launching transducer, or loudspeaker, enables the patient to exhale readily through a tube having its distal end opened to the atmosphere. Referring also to FIG. 20, the open end is shown coupled to an environment at substantially atmospheric pressure, another instrument such as a flowmeter, volume meter (i.e., spirometer) or a ventilator) collectively represented by a block designated by numeral 94.

Other embodiments are within the claims.

Other embodiments are within the following claims. For example, tube 16 (FIG. 1) could be 1.2 cm in diameter and 10 cm in length. In this case, the two transducers are preferably separated by 3.0 cm but transducer 18 is still located 2.0 cm from the airway opening. With the 10 cm tube, the propagation delay, τ, is made to correspond to seven time steps, i.e., τ=7Δt. This value of the propagation delay corresponds to a spatial step increment of about 0.2 cm.

Also, an algorithm other than the Ware-Aki algorithm could be used to uniquely determine the area-distance function, A(x), of the airway from h(t). Also, algorithms other than equation (8) above could be used to determine h(t) from the pressure field.

The attached appendix sets forth steps in a program for practicing the invention in a specific embodiment.

What is claimed is:

1. Apparatus for providing an output signal characteristic of a confined volume geometry comprising, a conduit having a predetermined length and an interior free of sound-absorbing or energy-absorbing material for exchanging acoustical energy with said confined volume, said conduit having an open first end adapted for communication with an opening in said confined volume and a second end separated from said first end by the length of the conduit, a launching transducer coupled to said conduit comprising means for launching acoustical energy into said conduit producing a first wave traveling towards said opening in said confined volume and the confined volume producing a second wave traveling away from said opening toward said second end in response to the first wave, the second wave having a wave field in said conduit representative of said confined volume geometry, a plurality to pressure-wave-sensing transducers mounted along a length of said conduit in spaced relationship for providing first and second transduced signals representative of said wave field, and a processor means coupled to said plurality of pressure-wave-sensing transducers including means for processing said first and second transduced signals in accordance with an algorithm that takes into account said first wave and said second wave to provide said output signal characteristic of said confined volume geometry.

2. A method for imaging a confined volume comprising, connecting an open first end of a conduit having an interior free of sound-absorbing or acoustic energy-absorbing material to an opening in said confined volume, propagating acoustical energy inside said conduit through said open first end and into said confined volume through said opening to produce a first wave traveling towards said opening in said confined volume and the confined volume producing a second wave traveling away from said opening towards said second end in response to the first wave the second wave having a wave field in said conduit representative of said confined volume geometry, transducing acoustic wave field parameters of said wave field at at least two spaced locations along said conduit to provide first and second transduced signals representative of said wave field, and processing said first and second transduced signals in accordance with an algorithm that takes into account said first wave and said second wave to provide an output signal representative of a characteristic of said confined volume.

3. Apparatus for providing an output signal characteristic of a confined volume geometry comprising, a conduit for exchanging acoustical energy with said confined volume, said conduit having a predetermined length a sidewall and an open first end in communication with an opening in said confined volume, a launching transducer coupled to launch acoustical energy through the sidewall of said conduit and produce an incident wave towards said opening in said confined volume and the confined volume producing a reflected wave in response to the incident wave, the reflected wave having a wave field in said conduit representative of said confined volume geometry, a plurality of pressure-wave-sensing transducers mounted along the length of said conduit in spaced relationship for providing first and second transduced signals representative of said wave field, and a processor means for providing high-pass filtering in processing said first and second transduced signals and providing, from said processing, said output signal characteristic of said confined volume geometry.

4. Apparatus for providing an output signal characteristic of a confined volume geometry comprising, a conduit for exchanging acoustical energy with said confined volume, said conduit having: a sidewall; an open first end in communication with an opening in said confined volume; and an open second end, a launching transducer coupled to said conduit for launching acoustical energy through the sidewall of said conduit to produce an incident wave towards said opening in said confined volume and said confined volume producing a reflected wave in response to the incident wave, the reflected wave having a wave field in said conduit representative of said confined volume geometry, a plurality of pressure-wave-sensing transducers mounted in spaced relationship along a length of said conduit for providing first and second transducers signal representative of said wave field, and a processor means for processing said transduced signals to provide, from said processing, a signal representative of the response of the incident wave to the confined volume and for high-pass filtering the response to produce said output signal characteristic of said confined volume geometry.

5. The apparatus recited in claim 4 where the high-pass filtering has a cutoff frequency approximately 250 Hz.

6. The apparatus as recited in claim 5 wherein said output signal is characteristic of cross-sectional area of said confined volume as a function of distance from said opening in said confined volume.

7. Apparatus as recited in claim 6 wherein said confined volume comprises an airway of an animal.

8. Apparatus as recited in claim 7 wherein said confined volume comprises an airway of a human.

9. Apparatus as recited in claim 7 wherein said airway comprises a pulmonary airway.

10. Apparatus as recited in claim 9 wherein said airway comprises a nasal airway.

11. Apparatus as recited in claim 10 wherein said airway comprises an oral airway.

12. Apparatus as recited in claim 5 wherein said conduit is less than or equal to 15 cm in length.

13. Apparatus as recited in claim 12 wherein said conduit is approximately 15 cm in length.

14. Apparatus as recited in claim 13 wherein said plurality of pressure wave sensing electroacoustical transducers are separated by approximately 10.25 cm.

15. Apparatus as recited in claim 12 wherein said conduit is approximately 10 cm in length.

16. Apparatus as recited in claim 15 wherein said plurality of pressure-wave-sensing transducers are separated by approximately 3.0 cm.

17. Apparatus in accordance with claim 5 wherein said confined volume is through a body passage input wherein said conduit comprises, a tube and a disposable device having an output end for snug engagement with said body passage input wall input end for snug engagement with said tube with good acoustic impedance matching and energy transmission.

18. Apparatus in accordance with claim 17 wherein said body passage is a nostril, ear canal, endotracheal tue or tracheostomy tube and said disposable device output end is sized for snug engagement with the input of said nostril.

19. Apparatus for providing an output signal characteristic of a confined volume geometry comprising, a conduit having an interior free of sound-absorbing or energy-absorbing material for exchanging acoustical energy with said confined volume, said conduit having: a predetermined length; a sidewall; an open first end adapted for communication with an opening in said confined volume; and, a second end separated from said first end by the conduit length, a launching transducer coupled to launch acoustical energy through the sidewall of said conduit producing a first wave traveling towards said opening in said confined volume and the confined volume producing a second wave traveling away from said opening toward said second end in response to the first wave, the second wave having a wave field in said conduit representative of the geometry of said confined volume, a plurality of pressure-wave-sensing transducers mounted along said length of the conduit in spaced relationship for providing first and second transduced signals representative of said wave field, and a processor means coupled to said plurality of pressure-wave-sensing transducers including means for processing said first and second transduced signals in accordance with an algorithm that takes into account said first wave and said second wave to provide said output signal characteristic of said confined volume geometry.

20. Apparatus for providing an output signal characteristic of a confined volume geometry comprising, a conduit for exchanging acoustical energy with said confined volume, said conduit having: a predetermined length; a sidewall; an open first end adapted for communication with an opening in said confined volume; and, a second end separated from said first end by the conduit length, a launching transducer coupled to launch acoustical energy through the sidewall of said conduit for launching acoustical energy into said conduit producing an incident wave towards said opening in said confined volume and said confined volume producing a reflected wave in response to the incident wave, the reflected wave having a wave field in said conduit representative of the geometry of said confined volume, a plurality of pressure-wave-sensing transducers mounted along said conduit length in spaced relationship for providing first and second transduced signals representative of said wave field, and a processor means coupled to said plurality of pressure-wave-sensing transducers for processing said first and second transduced signals to provide said output signal characteristic of said confined volume geometry, wherein said confined volume is characterized by cross-sectional area as a function of distance from said opening in said confined volume and said processor means provides as said output signal an area signal that is characteristic of cross-sectional area of said confined volume as a function of distance from said opening in said confined volume, wherein said conduit is less than or equal to 15 cm in length.

21. Apparatus in accordance with claim 20 wherein said conduit is substantially 15 cm in length.

22. Apparatus in accordance with claim 21 wherein said plurality of pressure wave sensing electroacoustical transducers are separated by substantially 10.52 cm.

23. Apparatus in accordance with claim 21 wherein said conduit is substantially 10 cm in length.

24. Apparatus in accordance with claim 23 wherein said plurality of pressure wave sensing transducers are separated by substantially 3.0 cm.

25. A method for imaging a confined volume comprising:
- connecting an open first end of a conduit to an opening in said confined volume;
- propagating acoustical energy into a sidewall of the conduit, through said open first end, and into said confined volume through said opening to establish a pressure field in said conduit representative of said confined volume; and
- transducing acoustic wave field parameters of said pressure field at a plurality of spaced locations along said conduit; and
- processing said transduced parameters to provide a response of the confined volume to the propagating acoustical energy and high-pass filtering the response to provide the output signal representative of said confined volume.

26. The method recited in claim 25 wherein the conduit is formed with a second end and wherein the second end of the conduit is open.

27. Apparatus for providing an output Signal characteristic of a confined volume geometry comprising,
- a conduit for exchanging acoustical energy with said confined volume,
- said conduit having a predetermined length and an open first end adapted for communication with an opening in said confined volume and a second end separated from said first end by the length of the conduit,
- a launching transducer coupled to said conduit for launching acoustical energy into said conduit producing an incident wave towards said opening in said confined volume and the confined volume producing a reflected wave in response to the incident wave, the reflected wave having a wave field in said conduit representative of said confined volume geometry,
- a Plurality of pressure-wave-sensing transducers mounted along said length of the conduit in spaced relationship for providing first and second transduced signals representative of said wave field, and
- a processor means coupled to said plurality of pressure-wave-sensing transducers for processing said first and second transduced signals produced in response to the incident wave, the reflected wave and any rereflected wave from the second end to provide a signal representative of an impulse response of the geometry and to provide said output signal characteristic of said confined volume geometry,
- wherein said confined volume is characterized by cross-sectional area as a function of distance from said opening in said confined volume and said processor means provides as said output signal an area signal that is characteristic of cross-sectional area of said confined volume as a function of distance from said opening in said confined volume.

28. Apparatus as recited in claim 27 wherein said conduit is less than 15 cm in length.

29. Apparatus as recited in claim 28 wherein said conduit is approximately 10 cm in length.

30. Apparatus as recited in claim 29 wherein said first and second pressure-wave-sensing transducers are separated by approximately 3.0 cm.

31. Apparatus as recited in claim 27 wherein said conduit is approximately 15 cm in length.

32. Apparatus as recited in claim 31 wherein said first and second pressure-wave-sensing transducers are separated by approximately 10.25 cm.

33. A method for imaging a confined volume comprising:
- connecting an open first end of a conduit to an opening in said confined volume;
- propagating acoustical energy inside said conduit, through said open first end, and into said confined volume through said opening to establish a pressure field in said conduit representative of said confined volume;
- transducing acoustic wave field parameters of said pressure field at a plurality of spaced locations along said conduit to produce signals representative of both incident and reflected waves; and
- processing said transduced parameters produced in response to the incident wave, the reflected wave and any rereflected wave from a second end of the conduit to provide a signal representative of an impulse response of the confined volume and providing said output signal characteristic of said confined volume geometry and providing an output signal representative of said confined volume geometry,
- wherein said confined volume is characterized by cross-sectional area as a function of distance from said opening in said confined volume and said output signal is representative of cross-sectional area of said confined volume as a function of distance from said opening in said confined volume.

* * * * *